(12) United States Patent
Abunassar

(10) Patent No.: US 9,028,541 B2
(45) Date of Patent: May 12, 2015

(54) STENT WITH ACTIVELY VARYING RING DENSITY

(75) Inventor: Chad Abunassar, San Francisco, CA (US)

(73) Assignee: Abbott Cardiovascular Systems Inc.

( * ) Notice: Subject to any disclaimer, the term of this patent is extended or adjusted under 35 U.S.C. 154(b) by 0 days.

(21) Appl. No.: 13/552,490

(22) Filed: Jul. 18, 2012

(65) Prior Publication Data
US 2014/0025157 A1 Jan. 23, 2014

(51) Int. Cl.
*A61F 2/06* (2013.01)
*A61F 2/915* (2013.01)

(52) U.S. Cl.
CPC ......... *A61F 2/915* (2013.01); *A61F 2002/9155* (2013.01); *A61F 2002/91558* (2013.01); *A61F 2002/91566* (2013.01); *A61F 2002/91575* (2013.01); *A61F 2230/0054* (2013.01)

(58) Field of Classification Search
USPC ............................................... 623/1.15–1.16
See application file for complete search history.

(56) References Cited

U.S. PATENT DOCUMENTS

| | | | |
|---|---|---|---|
| 5,843,175 A | 12/1998 | Frantzen | |
| 6,299,635 B1 | 10/2001 | Frantzen | |
| 2003/0176914 A1 | 9/2003 | Rabkin | |
| 2006/0224234 A1 | 10/2006 | Jayaraman | |
| 2007/0150046 A1 | 6/2007 | Meyer | |
| 2007/0276464 A1* | 11/2007 | Valencia et al. | 623/1.15 |
| 2011/0238156 A1 | 9/2011 | Tischler | |

OTHER PUBLICATIONS

International Search Report dated Aug. 7, 2013, PCT/US2013/039116.

* cited by examiner

*Primary Examiner* — Thomas J Sweet
*Assistant Examiner* — Tiffany Shipmon
(74) *Attorney, Agent, or Firm* — Fulwider Patton LLP; Jonathan Feuchtwang

(57) ABSTRACT

A stent and method comprising inserting within a vessel an unexpanded stent that includes a first zone comprising a plurality of adjacent ring elements, not less than three in number, that are distributed along the stent with a first spacing, and a second zone comprising a plurality of adjacent ring elements that are distributed along the stent with a second spacing, and expanding the stent to cause the plurality of ring elements in the first zone to redistribute to a third spacing that is smaller than the first spacing and to cause ring elements in the second zone to distribute to a fourth spacing larger than the first spacing.

14 Claims, 9 Drawing Sheets

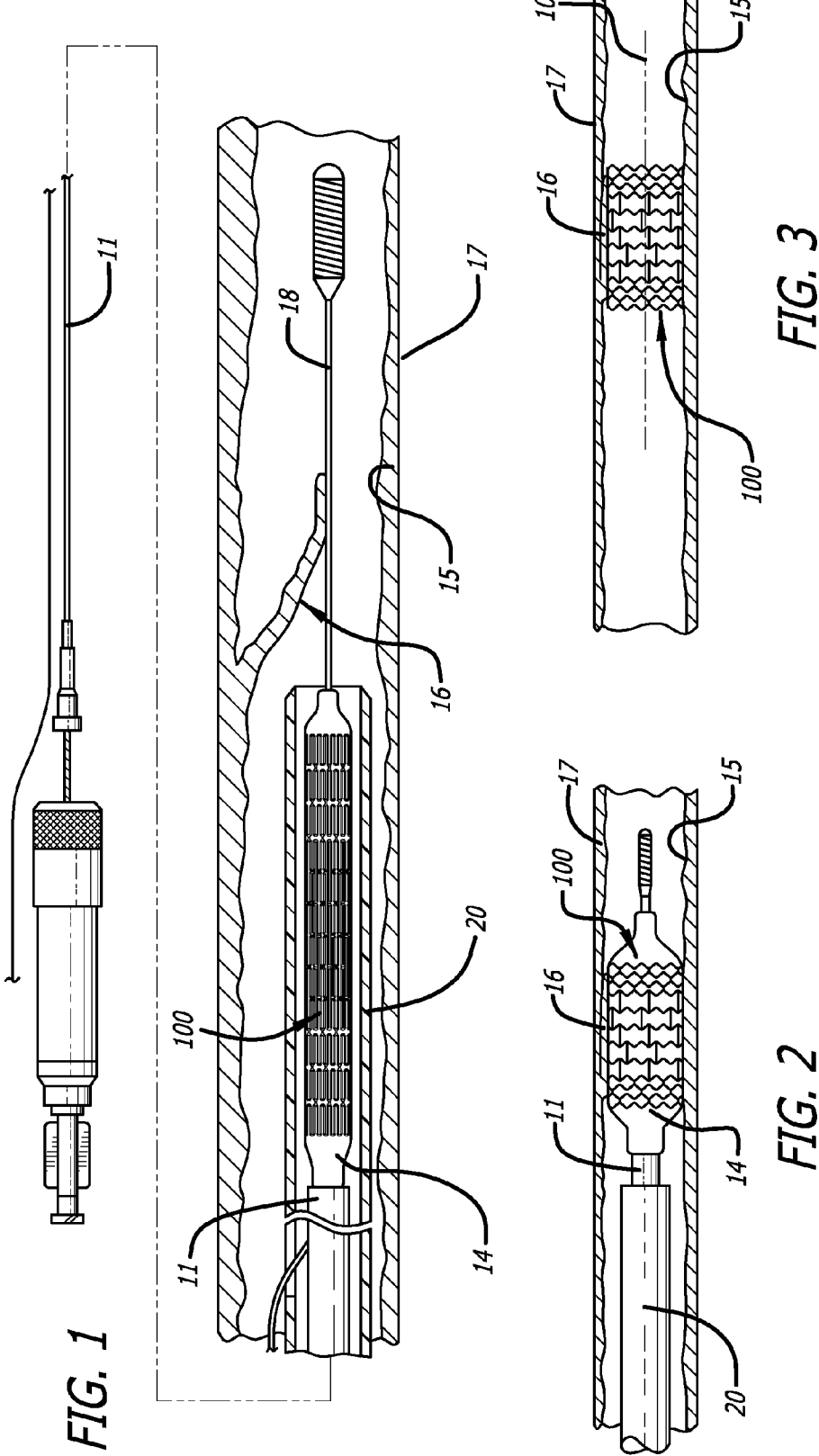

STENT WITH ACTIVELY VARYING RING DENSITY

BACKGROUND

The present invention relates to stents having a radial stiffness that varies along the length of the stent. Specifically, the invention relates to a stent that actively changes the density of rings in different zones along the axial length of the stent when the stent is expanded from a compressed condition to an expanded condition.

Surgical stents have long been known which can be surgically implanted into a body lumen, such as an artery, to reinforce, support, repair or otherwise enhance the performance of the lumen. For example, in cardiovascular surgery it is often desirable to place a stent in the coronary artery at a location where the artery is damaged or is susceptible to collapse. The stent, once in place, reinforces that portion of the artery allowing normal blood flow to occur through the artery. One form of stent which is particularly desirable for implantation in arteries and other body lumens is a cylindrical stent which can be radially expanded from a first smaller diameter to a second larger diameter. Such radially expandable stents can be inserted into the artery by being located on a catheter and introduced internally through the arterial pathways of the patient until the unexpanded stent is located where desired. The catheter is fitted with a balloon or other expansion mechanism which exerts a radial pressure outward on the stent causing the stent to expand radially to a larger diameter. Such expandable stents exhibit sufficient rigidity after being expanded that they will remain expanded after the catheter has been removed. An example of a stent known in the art is shown in FIG. 4 and FIG. 5. With initial reference to FIG. 4, the stent 50 shown there generally comprises a plurality of radially expandable cylindrical elements or rings 52 disposed generally coaxially along the axis 2 of the stent and interconnected by elements 54, 56 disposed between adjacent cylindrical elements. While FIG. 4 shows the stent 50 in a compressed or unexpanded condition suitable for delivery into the vasculature of a patient, FIG. 5 shows the same stent 50 in an expanded condition after placement and expansion in the vasculature.

Yet, known prior art stents suffer from a variety of drawbacks when certain types of deficiency or damage in an artery is encountered by a surgeon. For example, a surgeon may encounter an arterial situation where a stent is required to have greater radial support stiffness at the ends of the stent, and less radial support stiffness in the middle between the two ends. Another situation may be encountered requiring a stent having a greater radial support stiffness in the middle, and less radial support stiffness at the ends.

Certain stents have been developed to satisfy these requirements, but they suffer from drawbacks. For example, one approach describes a stent with greater radial support stiffness in the middle of the stent, wherein the struts are made thicker in the middle of the stent and thinner towards the ends. Another approach describes a stent with varying radial strength, wherein the desired effect is accomplished by increasing the width of the struts, or increasing the length of a cylindrical element. Yet another approach describes a stent in which the structural members are provided with regions having different widths, and tapering widths of selected segments. However, these solutions may result in a stent that is expensive to manufacture, and has non-uniform bending characteristics about the longitudinal axis and this latter aspect may introduce complications during delivery. Yet another approach describes a stent of differentiated stiffness that is achieved with the use of a superelastic material that transitions between a relatively soft and malleable phase to a stiffer phase at a transition temperature that is adjustable along the length of the stent. By differentially adjusting the transition temperature of different portions of the stent, a differentiation in the stiffness of the structure is achieved upon the stent being subjected to body temperature. However, this solution entails complex differentiated metallurgical application in a single stent in order to achieve the desired result.

Thus there is a need in the art for a simple and effective stent that possesses varying degrees of radial support stiffness over its length, that is easy to manufacture, and has substantially uniform longitudinal flexibility. The present invention addresses these and other needs.

SUMMARY OF THE INVENTION

In a preferred embodiment, the invention is an expandable axially elongate stent comprising a plurality of undulating ring elements configured to be expandable from an unexpanded condition to an expanded condition, the ring elements being positioned one adjacent to another along an axis. Each ring element includes a plurality of struts having an orientation in relation to the axis and each strut is connected to an adjacent strut by a curved elbow. Each curved elbow has a concave portion and a convex portion. A first zone of the stent includes a plurality of ring elements, not less than three in number, and each ring element in the first zone is connected to an adjacent ring element in the first zone by a connector extending from a convex portion of one ring to a convex portion of an adjacent ring. Furthermore a second zone of the stent includes a plurality of ring elements, not less than three in number, and each ring element in the second zone is connected to an adjacent ring element in the second zone by a connector extending from a concave portion of one ring to a concave portion of an adjacent ring. As will be explained in greater detail below, this configuration has the result that, upon expansion, the first zone shortens in length and thereby increases the ring density, and hence the radial support stiffness, of the first zone. At the same time, upon expansion the second zone increases in length, and thereby decreases the ring density, and hence the radial support stiffness, of the second zone.

In one embodiment of the invention, the first zone may be an end zone of the stent, and the second zone may be a middle zone adjacent the first zone. (As used herein, the term "adjacent," as applied to both rings and zones, is used to mean one alongside another and not separated by an additional ring element.) Under this configuration, a third zone may be added adjacent the second zone, having the configuration of the first zone in which each of a plurality of ring elements in the third zone is connected to an adjacent ring element in the third zone by a connector extending from a convex portion of one ring to a convex portion of an adjacent ring. Under this configuration, the stent may have end zones that have a greater radial support stiffness than in the middle zone.

In yet another embodiment of the invention, the second zone may be an end zone of the stent, and the first zone may be a middle zone adjacent the second zone. Under this configuration, a third zone may be added adjacent the first zone, having the configuration of the second zone, in which each of a plurality of ring elements in the third zone is connected to an adjacent ring element in the third zone by a connector extending from a concave portion of one ring to a concave portion of an adjacent ring. Under this configuration, the stent may have two end zones that have a smaller radial support stiffness than in the middle zone.

Further embodiments include that the connectors in the first zone are oriented parallel to the stent axis, and the connectors in the second zone are oriented parallel to the stent axis. This parallel configuration allows an improved predictability over the final length of the sent after expansion compared with the unexpanded condition.

In yet further embodiments of the invention all the ring elements in the stent in an unexpanded condition are substantially similar to each other in geometric shape. This feature provides the stent with improved uniformity of flexion along the length of the stent. Additionally, and adding to the same effect, all the ring elements in the stent in an unexpanded condition may be distributed at substantially even spacing over the axial length of the stent In a another embodiment, the stent may include a second zone of the stent positioned adjacent the first zone and which includes a plurality of ring elements, not less than three in number, and each ring element in the second zone is connected to an adjacent ring element in the second zone by at least one connector extending from a concave portion of one ring to a convex portion of an adjacent ring. Additionally, the stent may include a third zone which includes a plurality of ring elements and each ring element in the third zone is connected to an adjacent ring element in the third zone by at least one connector extending from a convex portion of one ring to a convex portion of an adjacent ring. In a variation of this embodiment, the stent may include a third zone including a plurality of ring elements and each ring element is connected to an adjacent ring element in the third zone by at least one connector extending from a concave portion of one ring to a concave portion of an adjacent ring.

In a further embodiment, the invention may be a method for supporting the wall of a vessel. The method comprises inserting within the vessel an unexpanded stent comprising a plurality of undulating ring elements configured to be expandable from an unexpanded condition to an expanded condition. The stent includes a first notional zone comprising a plurality of adjacent ring elements, not less than three in number, that are distributed along the stent with a first spacing. As used herein, "spacing" means the distance from the axial centerpoint of one ring to the axial centerpoint of an adjacent ring. Preferably, the spacing between all rings in a zone may be substantially the same when the stent is in the unexpanded condition, but this is not a requirement of the term "spacing." The stent also includes a second notional zone comprising a plurality of adjacent ring elements, not less than three in number, that are distributed along the stent by a second spacing. The method further includes expanding the stent, and thereby, causing the plurality of ring elements in the first zone to redistribute to a third spacing that is smaller than the first spacing; and further, causing the plurality of ring elements in the second zone to redistribute to a fourth spacing that is larger than the second spacing.

In some embodiments, the step of causing the plurality of ring elements in the first zone to redistribute to a third spacing includes causing ring elements in an end zone of the stent to redistribute to the third spacing. Further, causing the plurality of ring elements in the second zone to redistribute to a fourth spacing includes causing ring elements in a middle zone adjacent the end zone to redistribute to the fourth spacing. By these steps, a stent may be configured to expand so that the rings in the end zones bunch together upon expansion to provide a stent with enhanced radial support stiffness in the end zones, whereas rings in the middle zone spread apart upon expansion to provide a stent with reduced radial support stiffness in the middle zone.

However, in an alternative embodiment, causing the plurality of ring elements in the first zone to redistribute to a third spacing includes causing ring elements in a middle zone of the stent to redistribute to the third spacing. Additionally, causing the plurality of ring elements in the second zone to redistribute to a fourth spacing includes causing ring elements in an end zone adjacent the middle zone to redistribute to the fourth spacing. By these steps, a stent may be configured to expand so that the rings in the end zone spread apart upon expansion to provide a stent with reduced radial support stiffness in the end zone, whereas rings in the middle zone bunch together upon expansion to provide a stent with increased radial support stiffness in the middle.

In yet a further variation of the method of the present invention, expanding the stent may be configured to cause the plurality of ring elements in a middle zone to substantially maintain the ring spacing in the middle zone, while the rings in an end zone are caused to reduce the ring spacing upon expansion. Under this configuration, a stent may have end zones that are caused to increase their ring density upon expansion, while the middle zone retains the same ring density upon expansion. Thus, the resulting expanded stent may have an end zone with enhanced radial support stiffness compared with the middle zone. This variation allows the physician to select a stent that will have, upon expansion, greater radial support stiffness in the middle zone than compared with the stent of the first embodiment in which the ring density in the middle zone decreases upon expansion.

Thus it may be seen that under the various embodiments of the invention, the geometric properties of the rings and their respective connector elements may be strategically utilized to provide a stent that actively reconfigures the spacing of ring elements in different zones of the stent to provide a stent with the desired ring densities, and hence different radial support stiffness, in different zones of the stent. In some embodiments, one or more end zones are given greater radial support stiffness than a middle zone, while in other embodiments, a middle zone may be given greater radial support stiffness than an end zone.

These and other advantages of the present invention will become apparent when read in conjunction with the figures and the detailed description of the preferred embodiments.

BRIEF DESCRIPTION OF THE DRAWINGS

FIG. 1 is an elevational view, partially in section, of a stent embodying features of the invention which is mounted on a delivery catheter and disposed within a damaged artery.

FIG. 2 is an elevational view, partially in section, similar to that shown in FIG. 1 wherein the stent is expanded within a damaged artery, pressing the damaged lining against the arterial wall.

FIG. 3 is an elevational view, partially in section showing the expanded stent within the artery after withdrawal of the delivery catheter.

DETAILED DESCRIPTION OF THE PREFERRED EMBODIMENTS

Figures 4, 5:
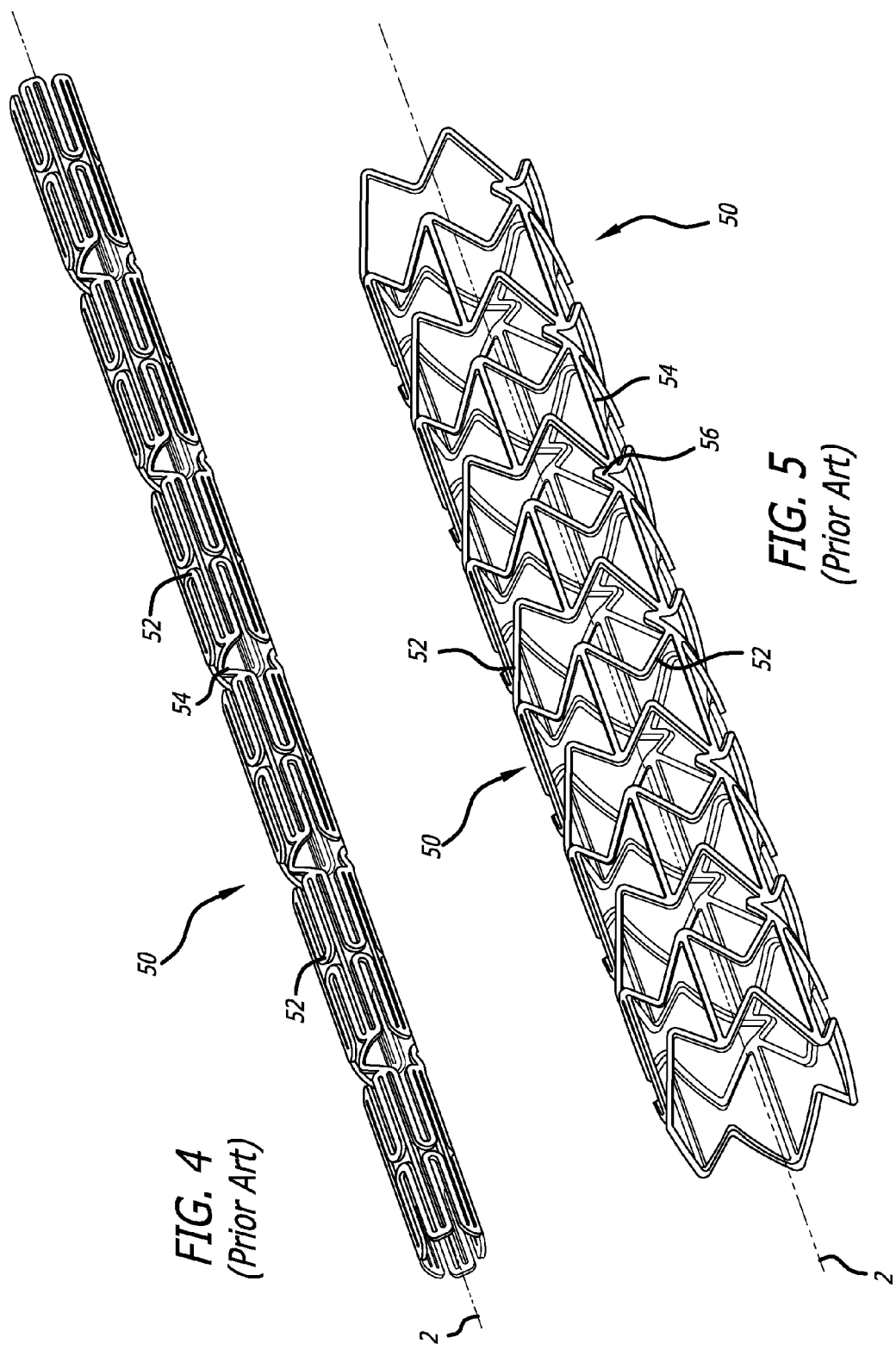
FIG. 4 is a perspective view of a known expandable stent, shown in an unexpanded condition.
FIG. 5 is a perspective view of the known stent of FIG. 4, shown in an expanded condition.

With reference to the figures, a stent is described having features of the present invention.

As an initial explanation, FIG. 1 illustrates a stent 100 incorporating features of the invention which is mounted onto a delivery catheter 11. The stent generally comprises a plurality of radially expandable cylindrical elements 112 disposed generally coaxially and interconnected by elements 124, 126 disposed between adjacent cylindrical elements. (Better seen in FIGS. 6 and 7.) The delivery catheter 11 has an expandable portion or balloon 14 for expanding of the stent 100 within an artery 15. The artery 15, as shown in FIG. 1, has a dissected lining 16 which has occluded a portion of the arterial passageway. While this dissection is one possible defect that may be repaired with the stent of the current invention, its use is not so limited, but may also, for example, be used for treatment of arterial stenosis or plaque buildup. In areas with excess and varying plaque burden is found, a stent with varying radial stiffness along the axial length may be needed, a feature of the invention that is described more fully herein.

The delivery catheter 11 onto which the stent 100 is mounted, is essentially the same as a conventional balloon dilatation catheter used for angioplasty procedures. The balloon 14 may be formed of suitable materials such as polyethylene, polyethylene terephthalate, polyvinyl chloride, nylon and ionomers such as Surlyn® manufactured by the Polymer Products Division of the Du Pont Company. Other polymers may also be used. In order for the stent 100 to remain in place on the balloon 14 during delivery to the site of the damage within the artery 15, the stent 100 is compressed onto the balloon. A retractable protective delivery sleeve 20 may be provided to further ensure that the stent stays in place on the expandable portion of the delivery catheter 11 and prevent abrasion of the body lumen by the open surface of the stent 100 during delivery to the desired arterial location. Other means for securing the stent 100 onto the balloon 14 may also be used, such as providing collars or ridges on the ends of the working portion, i.e. the cylindrical portion, of the balloon.

In a preferred embodiment, the delivery of the stent 100 may be accomplished in the following manner. The stent 100 may be first mounted onto the inflatable balloon 14 on the distal extremity of the delivery catheter 11. The balloon 14 may be slightly inflated to secure the stent 100 onto the exterior of the balloon. The catheter-stent assembly may be introduced within the patient's vasculature in a conventional Seldinger technique through a guiding catheter (not shown). A guidewire 18 may be disposed across the damaged arterial section with the detached or dissected lining 16 and then the catheter-stent assembly may be advanced over a guidewire 18 within the artery 15 until the stent 100 may be directly under the detached lining 16. The balloon 14 of the catheter may be expanded, expanding the stent 100 against the artery 15, which is illustrated in FIG. 2. While not shown in the drawing, the artery 15 is preferably expanded slightly by the expansion of the stent 100 to seat or otherwise fix the stent 100 to prevent movement. In some circumstances during the treatment of stenotic portions of an artery, the artery may have to be expanded considerably in order to facilitate passage of blood or other fluid therethrough.

In one embodiment of the invention, the stent 100 may serve to hold open the artery 15 after the catheter 11 is withdrawn, as illustrated by FIG. 3. Due to the formation of the stent 100 from an elongated tubular member, the undulating component of the cylindrical elements of the stent 100 may be relatively flat in transverse cross-section, so that when the stent is expanded, the cylindrical elements 112 are pressed into the wall of the artery 15 and as a result do not interfere with the blood flow through the artery 15. The cylindrical elements 112 of stent 100 which are pressed into the wall of the artery 15 will eventually be covered with endothelial cell growth which further minimizes blood flow interference. The undulating portion of the cylindrical sections 112 provide good tacking characteristics to prevent stent movement within the artery. Furthermore, the closely spaced cylindrical elements 112 at regular intervals provide uniform support for the wall of the artery 15, and consequently are well adapted to tack up and hold in place small flaps or dissections in the wall of the artery 15 as illustrated in FIGS. 2 and 3.

Figure 6:
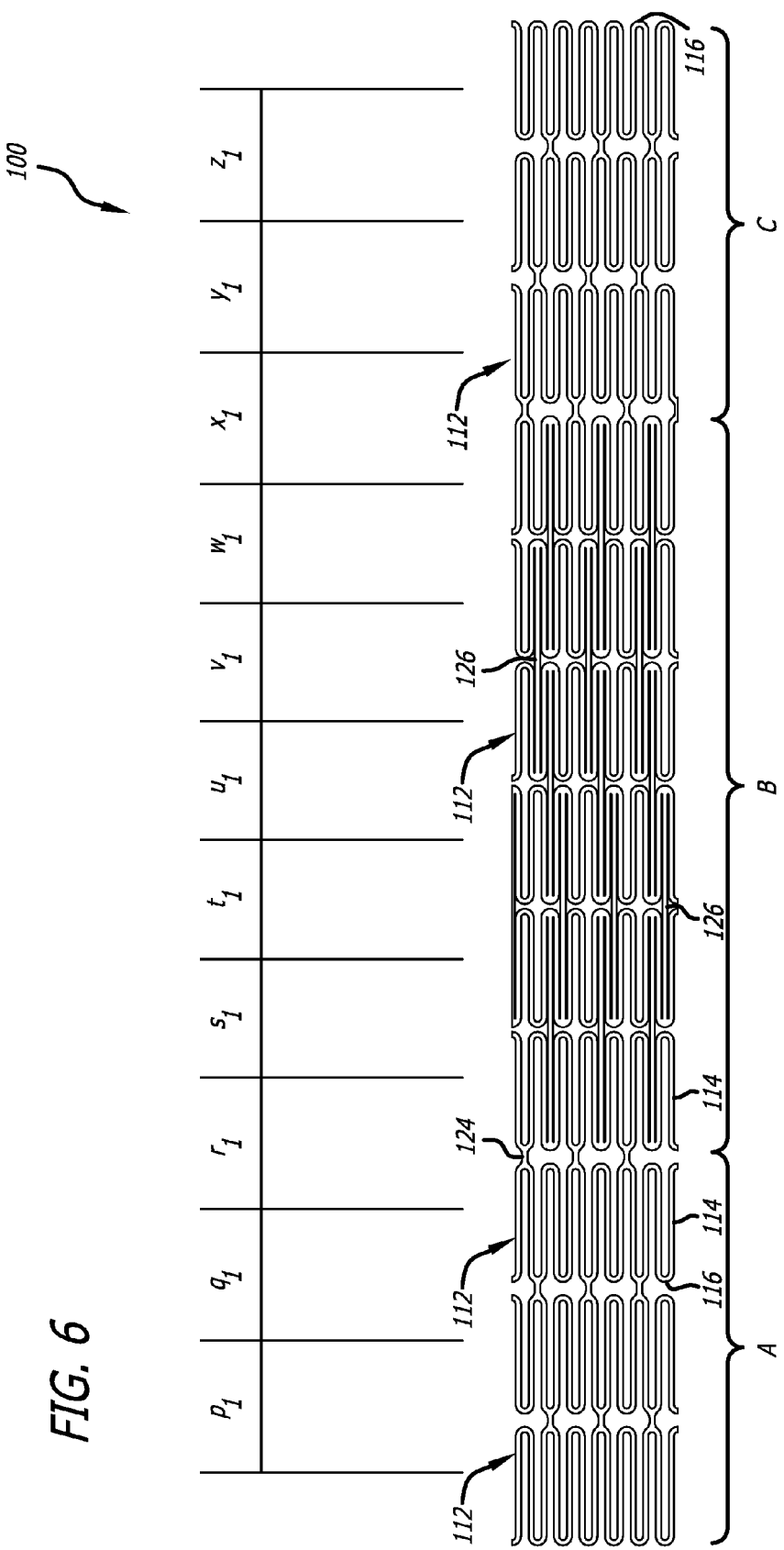
FIG. 6 is a schematic "rolled out" view (in which a planar view is shown of a cylindrical surface) of a preferred embodiment of a cylindrical stent having features of the present invention, shown in an unexpanded condition.
Figure 7:
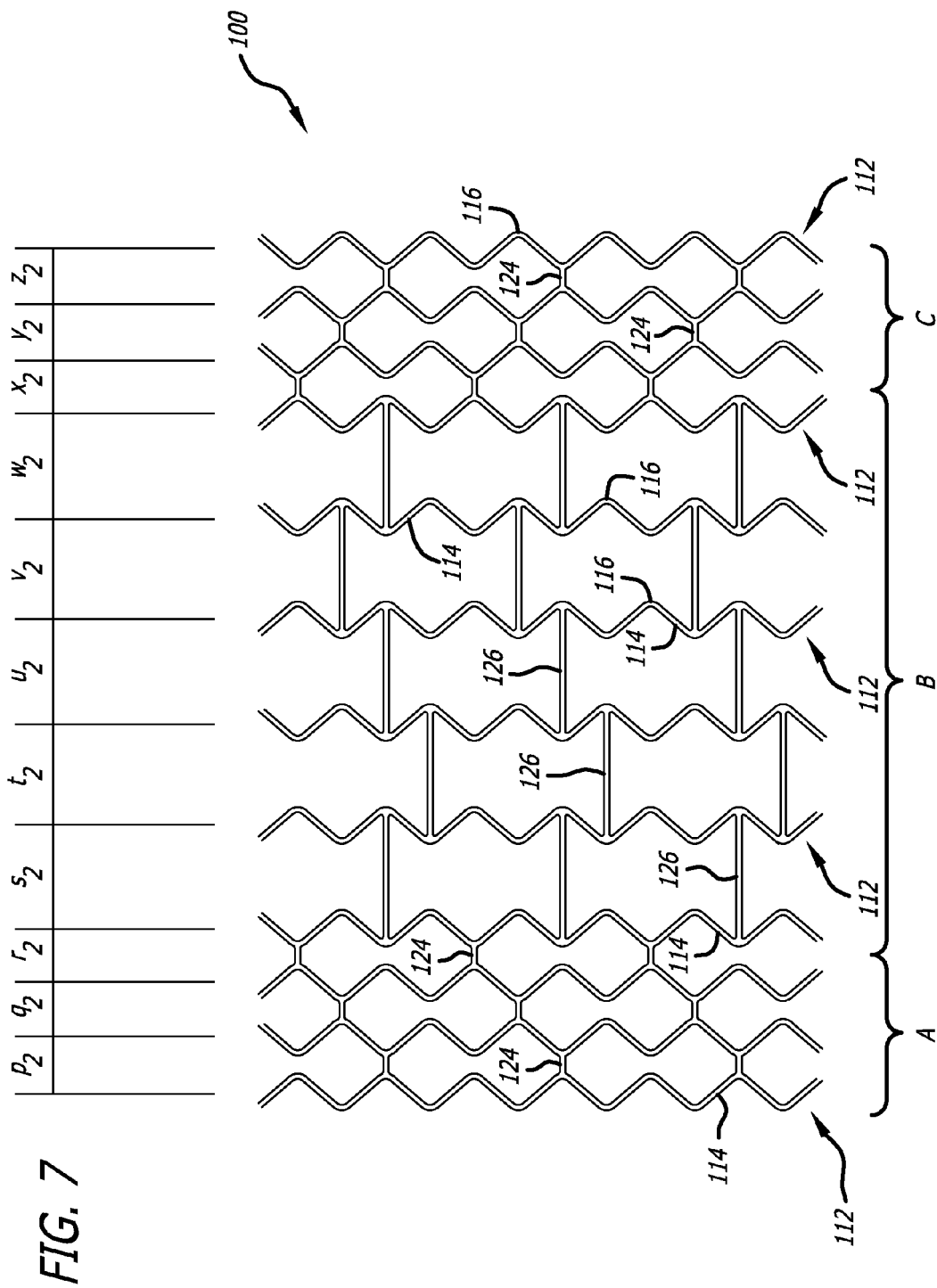
FIG. 7 is a schematic rolled out view of the stent of FIG. 6, shown in an expanded condition.

In preferred embodiments, exemplified in FIG. 6 through FIG. 11, a stent of the present invention includes a plurality of interconnected undulating rings 112, each configured according to known principles to be capable of being compacted to a reduced or unexpanded diameter suitable for delivery within the vasculature of a patient (as, for example, in FIG. 6), and of being expanded to an enlarged diameter suitable for scaffolding the vasculature at a desired location (as in FIG. 7). Each ring 112 includes a plurality of struts 114 having an orientation to the axis 101 (as seen in FIG. 3) of the stent and each strut is connected to an adjacent strut by a curved elbow 116. Due to this curve, each elbow 116 has a concave side 118 and a convex side 120 as seen in FIG. 12.

Figure 8:
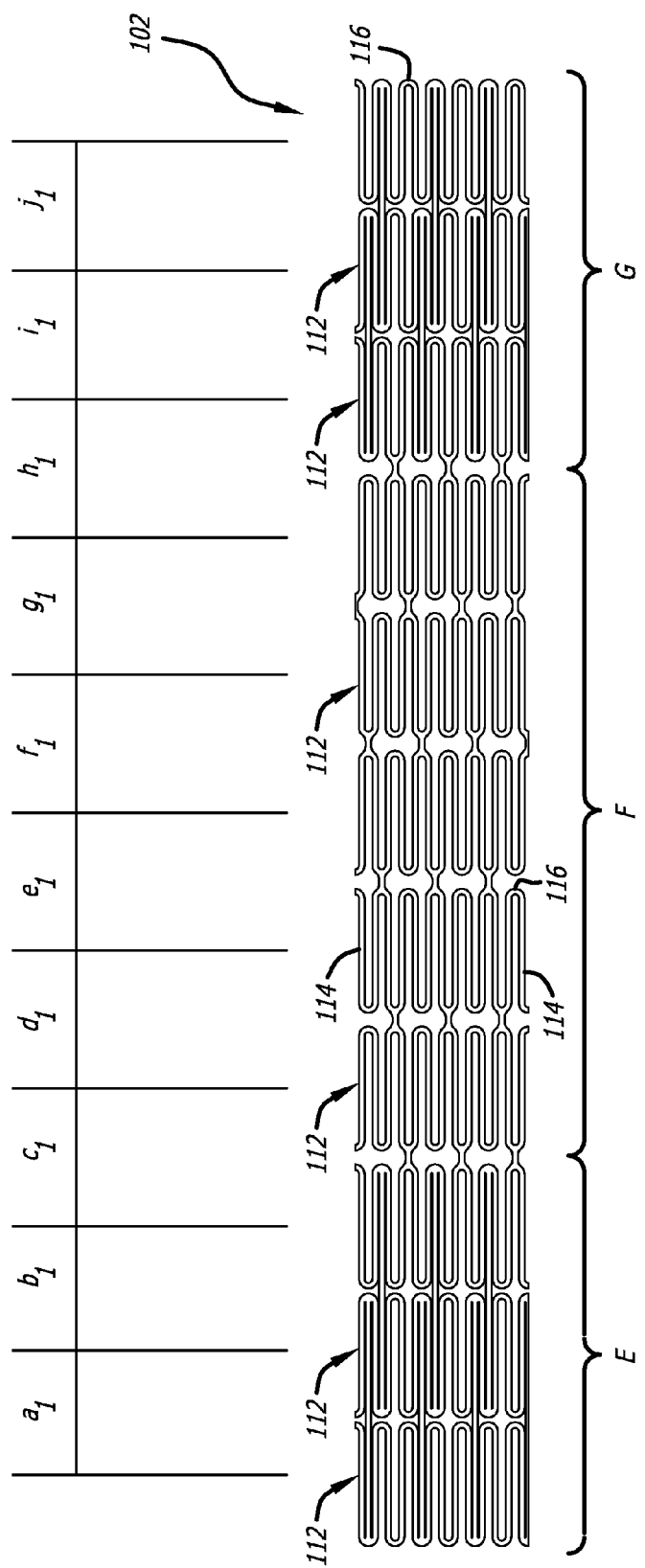
FIG. 8 is a schematic rolled out view of a further preferred embodiment of a stent having features of the present invention, shown in an unexpanded condition.
Figure 10:
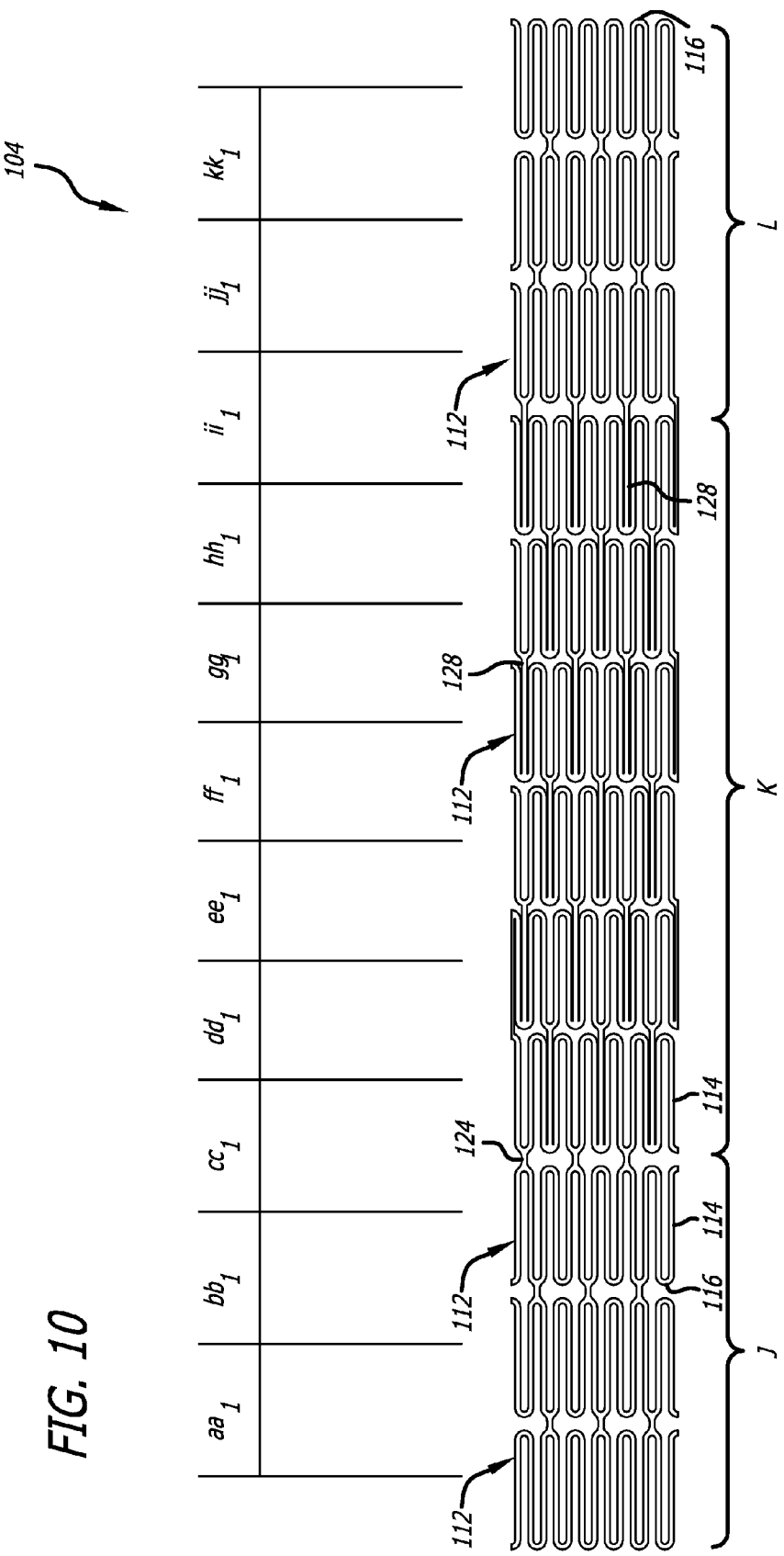
FIG. 10 is a schematic rolled out view of a yet a further preferred embodiment of a stent having features of the present invention, shown in an unexpanded condition.

In some embodiments, the rings 112 of the stent may all be substantially similar to each other in geometric shape, width, thickness, and metallurgical composition. As used herein, the term "substantially" similar in geometric shape, or otherwise, means that each dimensions on one ring are within 20% of the dimensions on another ring. In some embodiments, when the stent 100 is in an unexpanded diameter, the rings 112 may be distributed at substantially even spacing over the axial length of the stent (as seen in FIGS. 6, 8 and 10), thereby tending to provide the stent with a generally uniform axial flexibility for delivery within the vasculature of a patient.

FIGS. 6 and 7 exemplify a first preferred embodiment of a stent 100 of the present invention. This embodiment has two notional end zones A and C which are configured differently than a middle zone B positioned between the end zones. As will be described herein, the end zones A, C are configured so that, when expanded, they provide the stent with a greater radial support stiffness than the middle zone B. The term "radial support stiffness" is used herein to mean the ability to withstand radially inward forces per unit length of the stent. The term "end zone" is used herein to mean a zone of the stent that includes a terminal end of the stent. The term "middle zone" as used herein is used to mean a zone of the stent that is not an end zone.

FIG. 6 shows a schematic "rolled out" view of a cylindrical stent having features of the present embodiment, in which a planar view is shown of a cylindrical surface, of the geometric configuration of the cylindrical stent 100 of the present embodiment in an unexpanded condition. FIG. 7 shows (also in a rolled out view) the same stent 100 in an expanded condition, and is drawn to a smaller scale than FIG. 6.

The advantages of this embodiment are achieved as follows: With regard to the end zones A and C, each ring 112 in an end zone is connected to an adjacent ring by way of a connector 124 that connects a convex portion 120 of an elbow 116 of one ring 112 to a convex portion 120 of an elbow of an adjacent ring. This means that any two adjacent rings in the end zones are connected to each other across a small gap between the two rings and as a result the connector 124 is relatively short, or in some embodiments the connector 124 may have a negligible or zero notional "length" thus allowing the rings to connect to each other directly at convex points. This configuration of a direct connection between rings is also within the scope of the term connector 124 as used herein.

An end zone includes not less than three rings. The significance of such "convex to convex" connection is that, when the stent 100 is expanded, it adopts a configuration that is exemplified in FIG. 7, where it is seen that adjacent rings 112 that are connected to each other by a "convex to convex" connection configuration are necessarily drawn towards each other as the stent is expanded. Thus, for example, the distances p1, q1 and r1 separate the axial centerpoints of the rings in the left end zone of the unexpanded stent 10 shown in FIG. 6. When expanded to the configuration shown in FIG. 7, the axial centerpoints of the rings become separated by the distances p2, q2 and r2, each of which is necessarily smaller than the corresponding distances of the unexpanded configuration. The advantage of this effect will be described more fully below.

With regard to the middle zone B, each ring 112 in the middle zone is connected to an adjacent ring by way of a connector 126 that connects a concave side 118 of an elbow 116 on one ring 112 to a concave side of an elbow on an adjacent ring. This "concave to concave" connection configuration means that any two adjacent rings in the middle zone B are connected to each other across a relatively large space between structure on the two adjacent rings.

A middle zone B includes not less than three rings 112, and each ring in the middle zone is connected to an adjacent ring in the middle zone in such "concave to concave" configuration. The significance of such connection is that, when the stent 100 is expanded, it adopts a configuration exemplified in FIG. 7 in which adjacent rings that are connected to each other are necessarily caused to move away from each other when the stent is expanded. Thus, the distances s1, t1, u1, v1, w1 separate the axial centerpoints of the rings 112 in the middle zone of the unexpanded stent 10 shown in FIG. 6. When expanded to the configuration shown in FIG. 7, the axial centerpoints of the rings become separated by the distances s2, t2, u2, v2, w2 each of which is larger than the corresponding distances of the unexpanded configuration.

Thus, according to the description and explanation set forth above, the expansion of the stent 100 from the unexpanded condition to the expanded condition results in the following advantages. The end zones A, C of the stent contract in axial length. This contraction upon expansion has the effect of increasing the number of rings 112 per unit of axial length of the stent in the end zones compared with the unexpanded condition—and thereby increases the "ring density" in those zones compared with the ring density in the unexpanded condition. At the same time, the stent expansion results in the middle zone B increasing in axial length and therefore decreasing the ring density in that portion compared with the ring density in the unexpanded condition. As used herein, the term "ring density" means the number of rings per unit length of stent. It will be appreciated that an appropriate selection of the number of rings in the end zones and the middle zone can result in the overall length of the stent 100 remaining substantially constant during expansion because the shortening effect of the end zones A, C will be offset by the lengthening effect of the middle zone B. This provides a first advantage of the invention because despite the local redistribution of ring spacing over the length of the stent caused by expansion, the stent's overall length may nevertheless remain constant and thus may allow a physician to appropriately select the length of the unexpanded stent to match the length of the arterial lesion. Further, as a second advantage arising upon expansion of the stent, the increased ring density in the end zones A, C results in an increased radial support stiffness in those zones while the decreased ring density in the middle zone B causes a reduced radial support stiffness in that zone.

Figure 9:
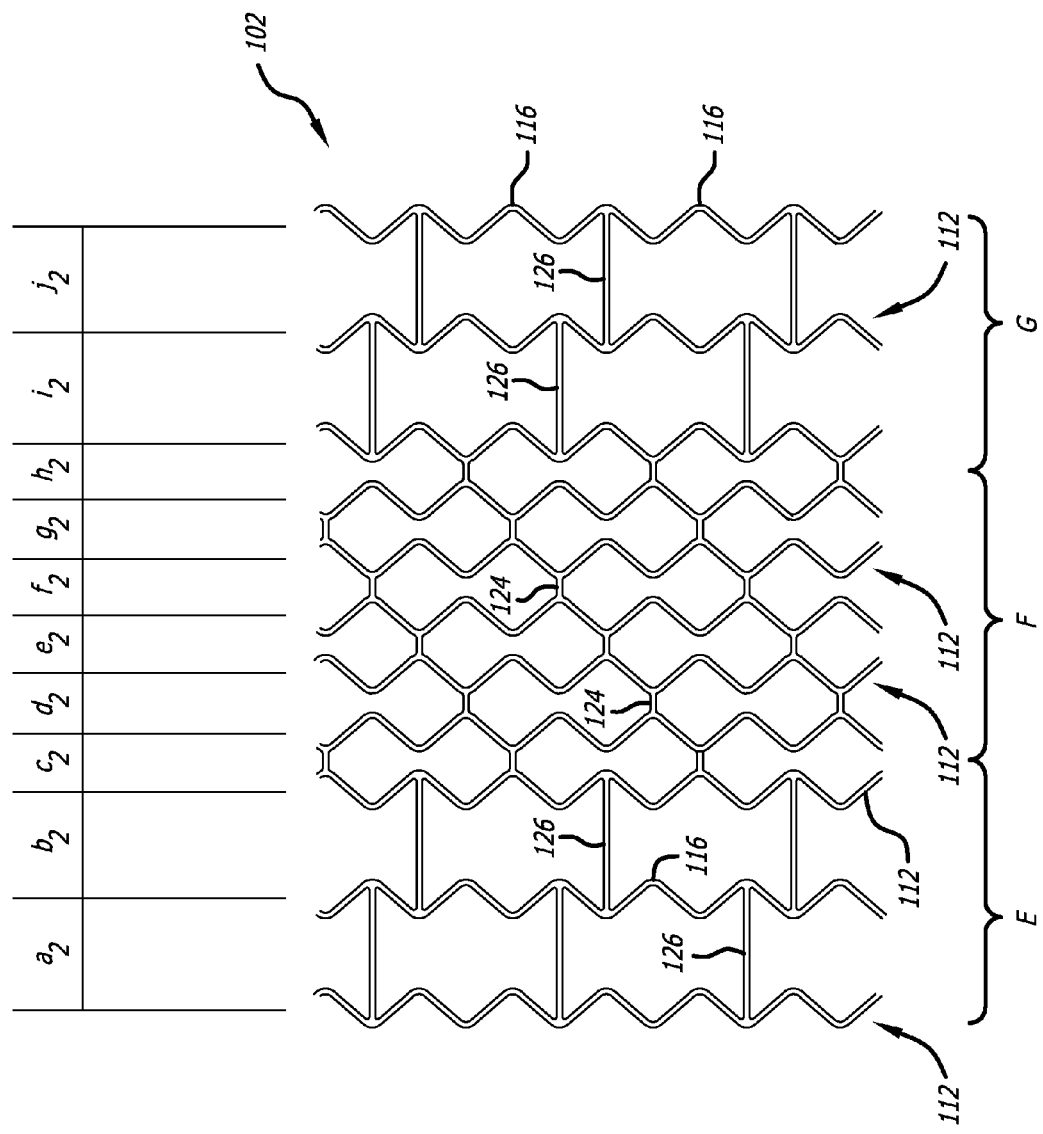
FIG. 9 is a schematic rolled out view of the stent of FIG. 8, shown in an expanded condition.

In a second preferred embodiment, exemplified in FIGS. 8 and 9, the stent 102 of this embodiment has two notional ends zones E and G which are configured differently than a middle zone F positioned between the end zones. The end zones E, G of this embodiment are configured as the middle zone B of the previous embodiment, and the middle zone F of this embodiment is configured as the end zones A, C of the previous embodiment. Thus, the middle zone F is configured so that, when expanded, it provides the stent with a greater radial support stiffness than the end zones E, G.

Described in detail, each ring 112 in the end zones is connected to an adjacent ring by way of a connector 126 that connects a concave side 118 of an elbow 116 on one ring 112 to a concave side of an elbow on an adjacent ring. This "concave to concave" connection configuration means that any two adjacent rings in an end zone are connected to each other across a large space between structure on the two rings. The end zones E, G include not less than three rings 112, and each ring in an end zones is connected to an adjacent ring in an end zone in such "concave to concave" configuration. The significance of such connection is that, when the stent 102 is expanded, it adopts a configuration exemplified in FIG. 9 in which adjacent rings that are connected to each other are necessarily caused to move away from each other when the stent is expanded. Thus, for example, the distances a1, b1 separate the axial centerpoints of the rings 112 in the end zone of the unexpanded stent 10 shown in FIG. 8. When expanded to the configuration shown in FIG. 9 (drawn to a smaller scale than FIG. 8), the axial centerpoints of the rings become separated by the distances a2, b2, each of which is larger than the corresponding distances of the unexpanded configuration.

With regard to the middle zone F, each ring 112 in the middle zone is connected to an adjacent ring by way of a connector 124 that connects a convex portion 120 of an elbow 116 of one ring 112 to a convex portion 120 of an elbow of an adjacent ring. This means that any two adjacent rings in the middle zone F of this embodiment are connected to each other across a small gap between the two rings and as a result the connector 124 is relatively short. The middle zone includes not less than three rings. The significance of such "convex to convex" connection is that, when the stent 102 is expanded, it adopts a configuration that is exemplified in FIG. 9, where it is seen that adjacent rings 112 that are connected to each other by a "convex to convex" connection configuration are necessarily drawn towards each other as the stent is expanded. Thus, the distances c1, d1, e1, f1, g1, and h1 separate the axial centerpoints of the rings in the center zone of the unexpanded stent 102 shown in FIG. 8. When expanded to the configuration shown in FIG. 9, the axial centerpoints of the rings become separated by the distances c2, d2, e2, f2, and h2, each of which is necessarily smaller than the corresponding distances of the unexpanded configuration.

This provides a first advantage of the invention of this embodiment of stent 102 because despite the local redistribution of ring spacing over the length of the stent caused by expansion, the stent's overall length may (if the correct number of rings are selected for each zone) nevertheless remain constant and thus may allow a physician to appropriately select the length of the unexpanded stent to match the length of the arterial lesion. Further, as a second advantage arising upon expansion of the stent, the decreased ring density in the end zones E, G results in a decreased radial support stiffness in those zones while the increased ring density in the middle zone F causes an increased radial support stiffness in that zone.

The advantages of this embodiment arise where the needs of the surgeon in relation to the vascular condition before her are the converse of those with regard to the use of the first embodiment.

Figure 11:
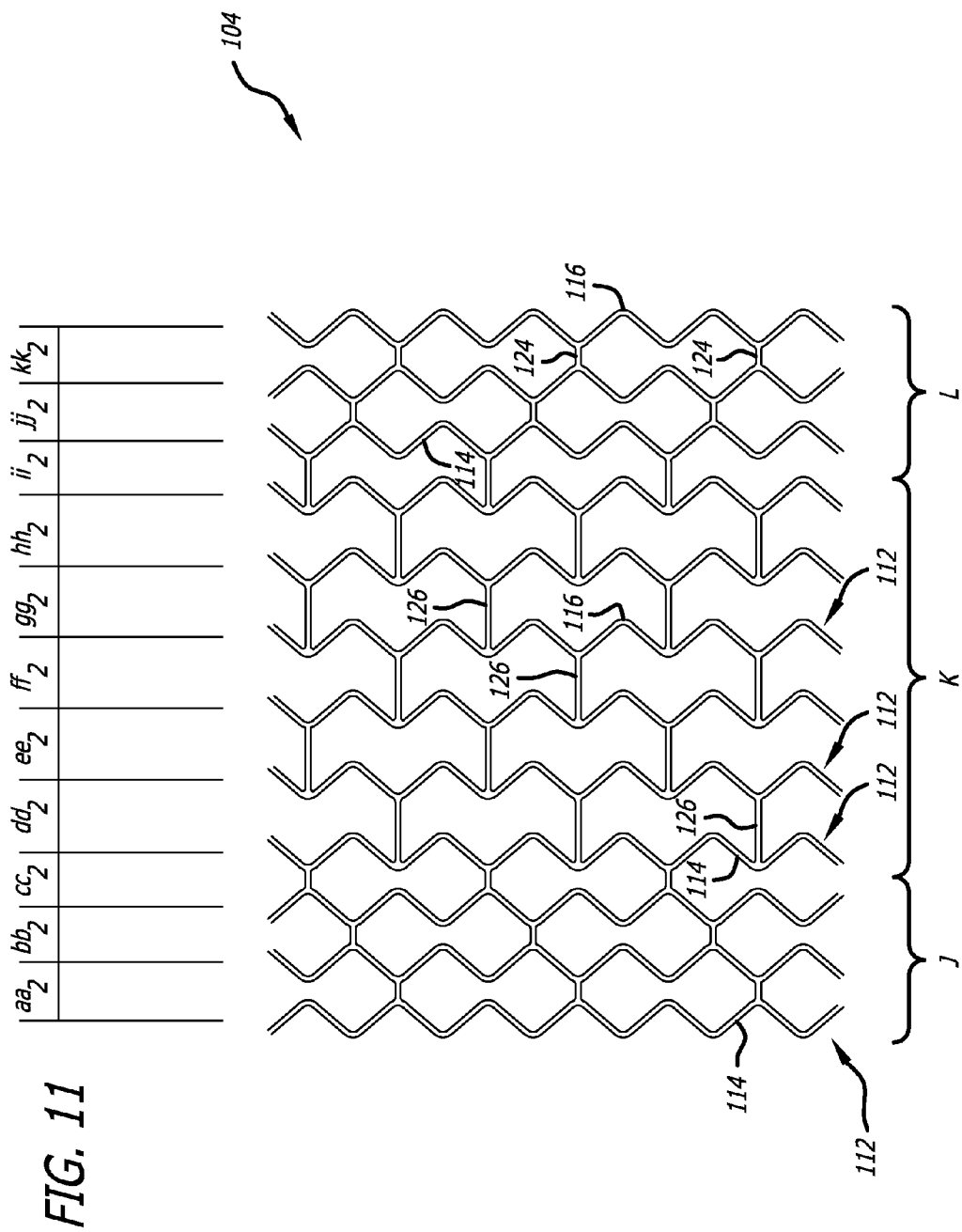
FIG. 11 is a schematic rolled out view of the stent of FIG. 10, shown in an expanded condition.
Figure 12:
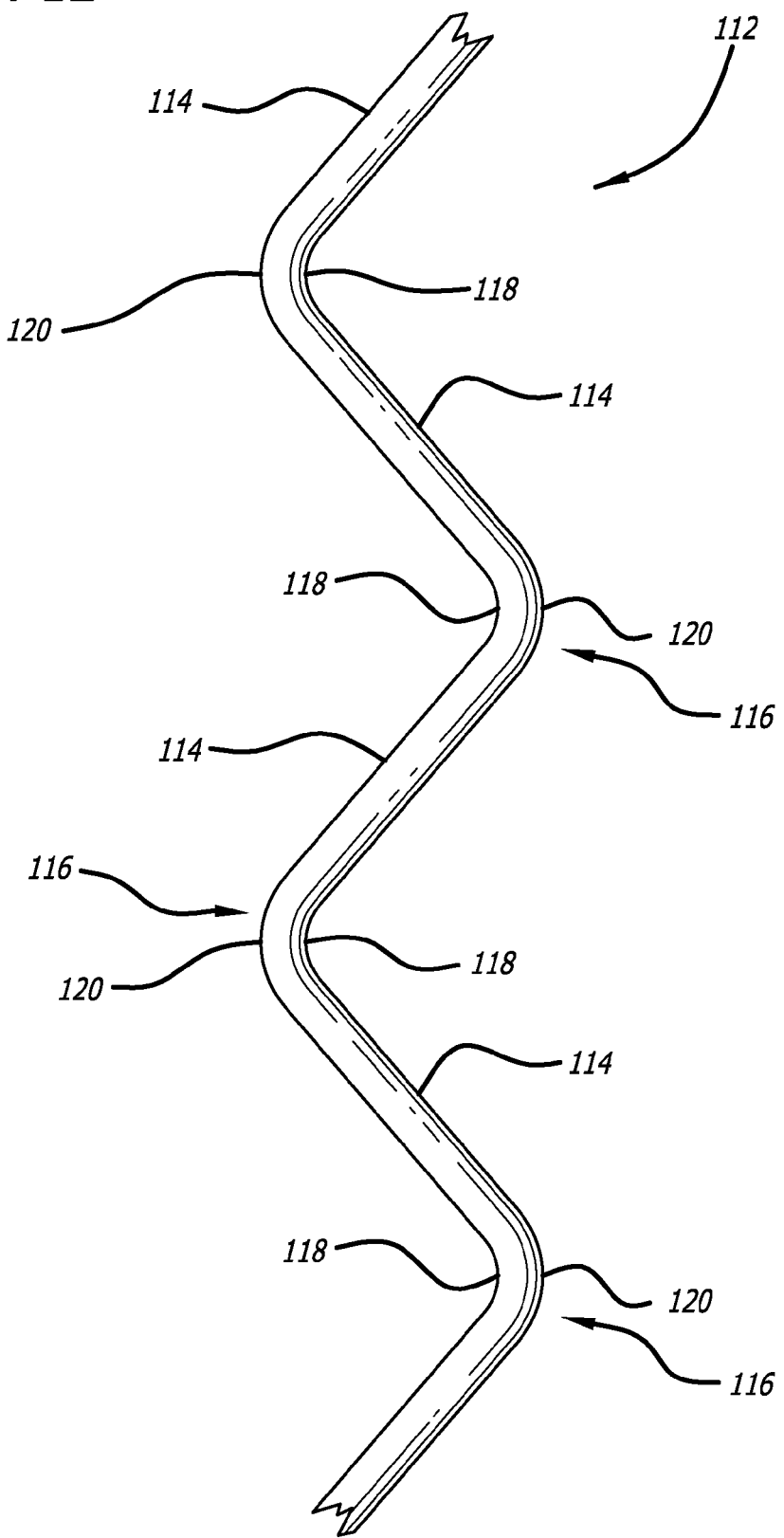
FIG. 12 is a detail view showing an aspect of the present invention.

In a third preferred embodiment, exemplified in FIGS. 10 and 11, the stent 104 of this embodiment has two notional ends zones J and L which are configured differently than a middle zone K positioned between the end zones. The end zones of this embodiment are configured the same as the end zones of the first embodiment 100 (FIGS. 6 and 7) but the middle zone K of this embodiment is configured so that, when expanded, it does not tend to lengthen or shorten.

Specifically, with regard to the middle zone K, each ring 112 in the middle zone is connected to an adjacent ring by way of a connector 128 that connects a convex portion 120 of an elbow 116 of one ring 112 to a concave portion 118 of an elbow of an adjacent ring. Preferably, the middle zone of this embodiment includes not less than three rings 112. The significance of such "convex to concave" connection is that, when the stent 104 is expanded, it adopts a configuration that is exemplified in FIG. 11, where it is seen that adjacent rings 112 that are connected to each other by a "convex to concave" connection configuration necessarily maintain the spacing between the rings as the stent is expanded. Thus, the distances aa1, and bb1 separate the axial centerpoints of the rings in the left end zone of the unexpanded stent 104 shown in FIG. 10. When expanded to the configuration shown in FIG. 11, the axial centerpoints of the rings become separated by the distances aa2, and bb2, each of which is substantially the same as the corresponding distances of the unexpanded configuration. This embodiment permits a stent that, upon expansion, has increased ring density in the end zones, and thus increased radial support stiffness in the end zones J, L compared to the middle zone K.

In a variation of the embodiment shown in FIG. 11, one of the end zones may, instead of being comprised of rings connected to each other by "convex to convex" connection, may be comprised of rings connected by "concave to concave" connection. It will be appreciated that, according to the principles of the invention, in this embodiment the stent will have a gradually decreasing radial stiffness extending from one end to the other. A first end zone will be radially stiffer than an adjacent middle zone, which in turn will be stiffer than a second end zone.

Thus, there is described an advantageous system and method that provides a solution to problems encountered in the prior art. The present invention may, of course, be carried out in other specific ways than those herein set forth without departing from the essential characteristics of the invention. For example, combinations of the different kinds of zone described may be combined with each other in sequences not expressly stated or illustrated, and thus, the present embodiments are to be considered in all respects as illustrative and not restrictive, while the scope of the invention is set forth in the claims that follow.

I claim:

1. An expandable axially elongate stent comprising:
   a plurality of undulating ring elements configured to be expandable from an unexpanded condition to an expanded condition, the ring elements being positioned one adjacent to another along an axis, wherein,
      each ring element includes a plurality of struts having an orientation in relation the axis and each strut is connected to an adjacent strut by a curved elbow; and
      each curved elbow has a concave portion and a convex portion,
      each ring element in the stent is connected to an adjacent ring element by a connector, wherein the connector is linear and has a first end and a second end and an entire length between the first end and the second end, and further wherein the connector is connected to a first ring element at the first end and is connected to a second ring element at the second end, and the entire length of the connector extends parallel with the axis;
   further wherein, a first zone of the stent includes a plurality of ring elements, not less than three in number, and each ring element in the first zone is connected to an adjacent ring element in the first zone by at least one connector extending from a convex portion of one ring to a convex portion of an adjacent ring; and
   further wherein, a second zone of the stent includes a plurality of ring elements, not less than three in number, and each ring element in the second zone is connected to an adjacent ring element in the second zone by at least one connector extending from a concave portion of one ring to a concave portion of an adjacent ring.

2. The stent of claim 1, wherein the first zone is an end zone of the stent.

3. The stent of claim 2, wherein the second zone is a middle zone adjacent the first zone.

4. The stent of claim 3, further wherein a third zone of the stent, adjacent the second zone, includes a plurality of ring elements, not less than three in number, and each ring element in the third zone is connected to an adjacent ring element in the third zone by at least one connector extending from a convex portion of one ring to a convex portion of an adjacent ring.

5. The stent of claim 1, wherein the second zone is an end zone of the stent.

6. The stent of claim 5, wherein the first zone is a middle zone adjacent the second zone.

7. The stent of claim 6, further wherein a third zone of the stent, adjacent the first zone, includes a plurality of ring elements, not less than three in number, and each ring element in the third zone is connected to an adjacent ring element in the third zone by at least one connector extending from a concave portion of one ring to a concave portion of an adjacent ring.

8. The stent of claim 1, wherein all the ring elements in the stent in an unexpanded condition are substantially similar to each other in geometric shape.

9. The stent of claim 1, wherein all the ring elements in the stent in an unexpanded condition are distributed at substantially even intervals over the axial length of the stent.

10. An expandable axially elongate stent comprising:
a plurality of undulating ring elements configured to be expandable from an unexpanded condition to an expanded condition, the ring elements being positioned one adjacent to another along an axis, wherein,
   each ring element includes a plurality of struts having an orientation in relation the axis and each strut is connected to an adjacent strut by a curved elbow; and
   each curved elbow has a concave portion and a convex portion, and
   each ring element in the stent is connected to an adjacent ring element by a connector, wherein the connector is linear and has a first end and a second end and an entire length between the first end and the second end, and further wherein the connector is connected to a first ring element at the first end and is connected to a second ring element at the second end, and the entire length of the connector extends parallel with the axis;
further wherein, a first zone of the stent includes a plurality of ring elements, not less than three in number, and each ring element in the first zone is connected to an adjacent ring element in the first zone by at least one connector extending from a convex portion of one ring to a convex portion of an adjacent ring; and
further wherein, a second zone of the stent positioned adjacent the first zone includes a plurality of ring elements, not less than three in number, and each ring element in the second zone is connected to an adjacent ring element in the second zone by at least one connector extending from a concave portion of one ring to a convex portion of an adjacent ring.

11. The stent of claim 10, further wherein a third zone of the stent includes a plurality of ring elements and each ring element in the third zone is connected to an adjacent ring element in the third zone by at least one connector extending from a convex portion of one ring to a convex portion of an adjacent ring.

12. The stent of claim 10, further wherein a third zone of the stent includes a plurality of ring elements and each ring element in the third zone is connected to an adjacent ring element in the third zone by at least one connector extending from a concave portion of one ring to a concave portion of an adjacent ring.

13. The stent of claim 10, wherein all the ring elements in the stent in an unexpanded condition are substantially similar to each other in geometric shape.

14. The stent of claim 10, wherein all the ring elements in the stent in an unexpanded condition are distributed at substantially even intervals over the axial length of the stent.

* * * * *